US006773427B2

(12) United States Patent
Takagi

(10) Patent No.: US 6,773,427 B2
(45) Date of Patent: Aug. 10, 2004

(54) INFUSION CONTAINER

(75) Inventor: Nobuo Takagi, Osaka (JP)

(73) Assignee: Nipro Corporation, Osaka (JP)

( * ) Notice: Subject to any disclaimer, the term of this patent is extended or adjusted under 35 U.S.C. 154(b) by 238 days.

(21) Appl. No.: 10/059,244

(22) Filed: Jan. 31, 2002

(65) Prior Publication Data

US 2002/0107500 A1 Aug. 8, 2002

(30) Foreign Application Priority Data

Feb. 5, 2001 (JP) ....................................... 2001-028056

(51) Int. Cl.[7] .......................... A61B 19/00; A61M 5/32; B65D 37/00; B65D 85/00; B65D 75/00

(52) U.S. Cl. ....................... 604/415; 604/408; 604/406; 206/0.5; 206/828; 222/211; 222/212

(58) Field of Search ................................ 604/403–410, 604/6.16, 4.01; 128/DIG. 24; 206/0.5, 438, 828; 220/200, 202, 203.01, 203.08, 203.11, 203.13–203.14; 141/301, 302, 329–30, 21–29; 222/206, 211–12, 566–70, 572, 544, 562–63

(56) References Cited

U.S. PATENT DOCUMENTS

| | | | | |
|---|---|---|---|---|
| 4,301,799 | A | * | 11/1981 | Pope, Jr. et al. |
| 6,358,236 | B1 | * | 3/2002 | DeFoggi et al. |
| 6,568,439 | B1 | * | 5/2003 | Se et al. |

FOREIGN PATENT DOCUMENTS

| | | | |
|---|---|---|---|
| EP | 0 968 732 | A2 | 1/2000 |
| JP | 9-19480 | A | 1/1997 |
| WO | 96/29113 | A1 | 9/1996 |
| WO | 99/62578 | A2 | 12/1999 |

* cited by examiner

*Primary Examiner*—Patricia Bianco
(74) *Attorney, Agent, or Firm*—Kubovcik & Kubovcik

(57) ABSTRACT

An infusion container comprising a communication port capable of being connected with a syringe, a container main body, a communication channel for providing communication between the inside of the container main body and the inner lumen of the communication port, and a sterilization filter provided in the communication channel, wherein the communication port is closed with a rubber stopper provided with a slit allowing the top end tip of the syringe to pass therethrough and the communication channel is closed with a closing means capable of being easily opened.

1 Claim, 3 Drawing Sheets

INFUSION CONTAINER

TECHNICAL FIELD OF THE INVENTION

This invention relates to an infusion container capable of having a drug solution aseptically injected into an inside of a main body of the container.

BACKGROUND OF THE INVENTION

Since a drug solution, for example, a vitamin preparation is denatured by heat, an infusion container in which the drug solution is contained can not be sterilized using high pressure steam. Conventionally, the drug solution which is denatured by heat is injected into an infusion container and mixed with another solution therein upon infusion treatment. When the drug solution is injected into the infusion container and mixed with the other solution therein, piercing an injection needle through a rubber stopper of a drug discharge port of the infusion container has been adopted. However, it is difficult to carry out such method of injection and mixing aseptically and there is a fear that bacteria will contaminate the infusion container.

In view of the above, as a medical container capable of injection and mixing of a drug solution aseptically, a medical container in which an injection port for mixing, i.e., a drug injection port, comprises a cylindrical port member, a rubber stopper for sealing the port member, a piercing part, a housing for providing communication between an inside thereof and an inside of the piercing part and connected to or formed by integral molding with the piercing part, a sterilization filter supported by the housing and an accommodation cover, has been proposed (Japanese Patent Laid-Open Publication No. 19480/1997). However, the medical container described above is disadvantageous because of occurrence of coring caused by piercing of the rubber stopper, an enlarged scale of the drug injection port due to the structure of the piercing part, or an increased cost caused by a large number of components.

This invention has been accomplished in view of the foregoing background and intends to provide an infusion container in which injecting and mixing of drugs can be performed aseptically, in which no coring is caused, having fewer parts, and having a compact structure.

SUMMARY OF THE INVENTION

Intense studies have been carried out by the inventor of the present invention in order to solve the foregoing problems. As a result, it was found that the problems can be solved by using a rubber stopper with a slit as the rubber stopper for sealing the port member, and the present invention was completed.

That is, this invention concerns an infusion container comprising a communication port capable of connecting with a syringe, a container main body, a communication channel for communicating the inside of the container main body with the communication port, and a sterilization filter provided in the communication channel, wherein an inner lumen of the communication port is closed with a rubber stopper provided with a slit which allows a top end tip of the syringe to pass therethrough and wherein the communication channel is closed by a closing means capable of being easily opened.

The closing means is disposed on a base end of the sterilization filter. The closing means preferably has a structure in which a film is welded weakly to the surface on a base end of an annular protrusion provided on an inner wall of a communication channel portion of the communication channel. Further, the sterilization filter preferably is sandwiched between the communication port and the communication channel portion.

DESCRIPTION OF THE DRAWINGS

Referring to the preferred embodiments and attached drawings, the infusion container of the present invention will hereinafter be described. However, the present invention is not limited to these embodiments.

DETAILED DESCRIPTION OF THE INVENTION

Figure 1:
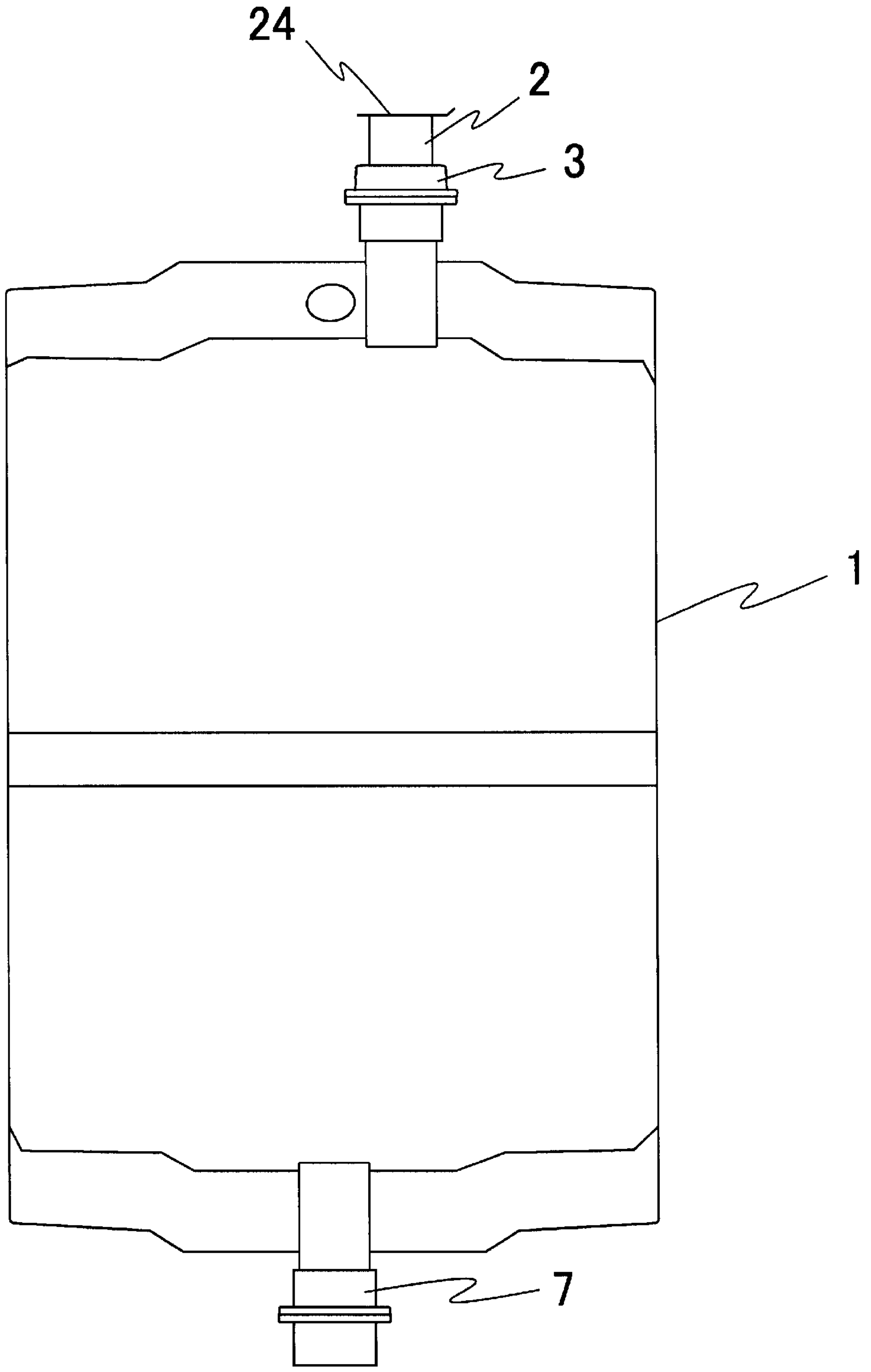
FIG. 1 is a plane view of an infusion container according to an embodiment of the present invention.
Figure 2:
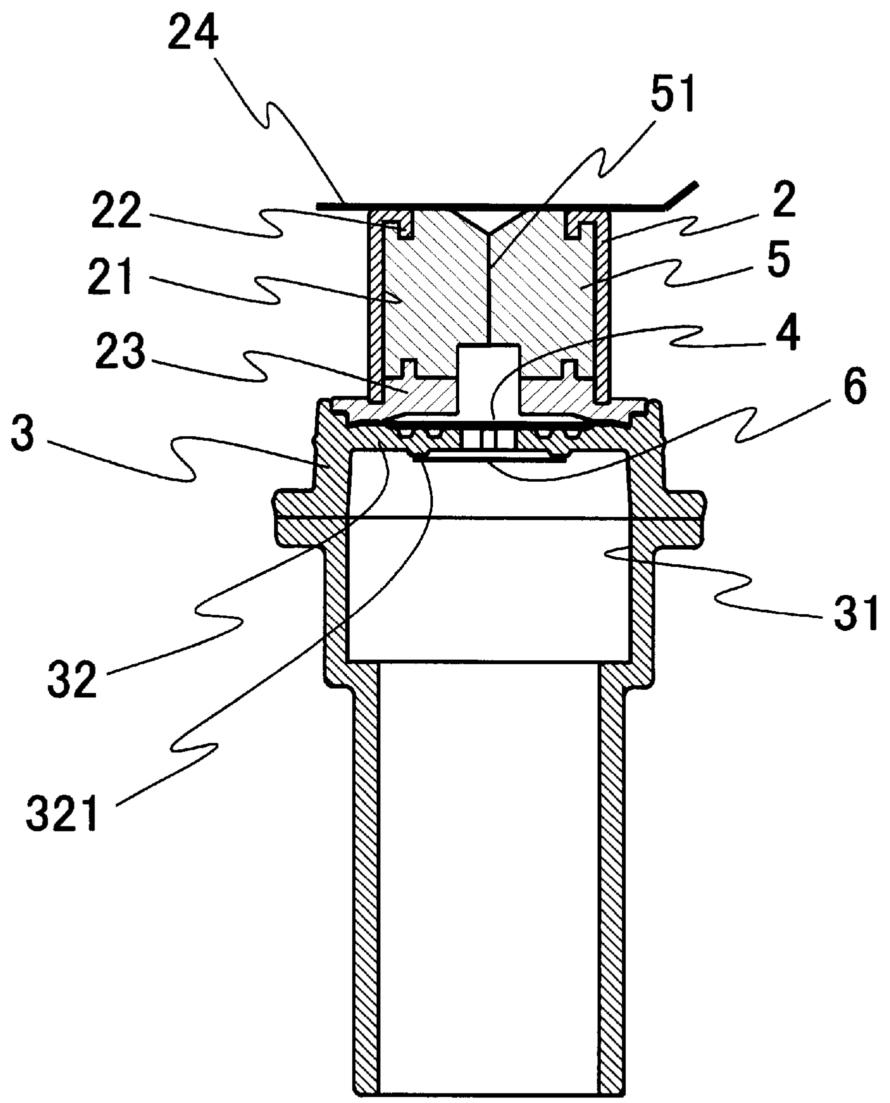
FIG. 2 is an enlarged cross sectional view of a main portion of the infusion container shown in FIG. 1.

As shown in FIG. 1 and FIG. 2, an infusion container of the present invention comprises a communication port 2 capable of connecting with a syringe (not illustrated), a container main body 1, and a communication channel 31 for providing communication between an inside of the container main body 1 and a inner lumen 21 of the communication port 2. The communication channel 31 is provided with a sterilization filter 4. The inner lumen 21 of the communication port 2 is closed with a rubber stopper 5 provided with a slit 51 which allows a top end tip of the syringe to pass therethrough. Further, the communication channel 31 is closed with a closing means 6 capable of being easily opened.

In the infusion container according to the present invention, the term "top end" means the end into which a drug solution is injected (upward in the drawing) and the term "base end" means the end from which a liquid in the infusion container is discharged (downward in the drawing).

The container main body 1 is a bag body generally made of polyethylene, polypropylene, polyester, polyvinyl chloride, ethylene-vinyl acetate copolymer or the like. A drug solution such as an amino acid preparation, glucose preparation, electrolyte preparation or physiological saline is contained in the container main body 1. The communication port 2 is connected to the top end of the container main body 1 by way of a communication channel portion 3. Further, a discharge port 7 is provided at the base end of the container main body 1.

The communication port 2 comprises a cylindrical member generally made of polyethylene, polypropylene, polyester, polyamide or the like. The inner lumen 21 of the communication port 2 is closed liquid-tightly with a rubber stopper 5. An annular protrusion 22 is formed at the top end on an inner wall of the communication port 2, and an annular protrusion 23 is formed at the base end on the inner wall of the communication port 2. The annular protrusion 22 is smaller than the annular protrusion 23 in a transverse direction of the communication port 2. The rubber stopper 5 is attached liquid-tightly in a space surrounded by the inner wall of the communication port 2 and the annular protrusions 22, 23. The annular protrusion 23 may be formed by integral molding with the communication port 2 or formed separately from the communication port 2 and subsequently integrated with the communication port 2 as shown in FIG. 2.

Figure 3:
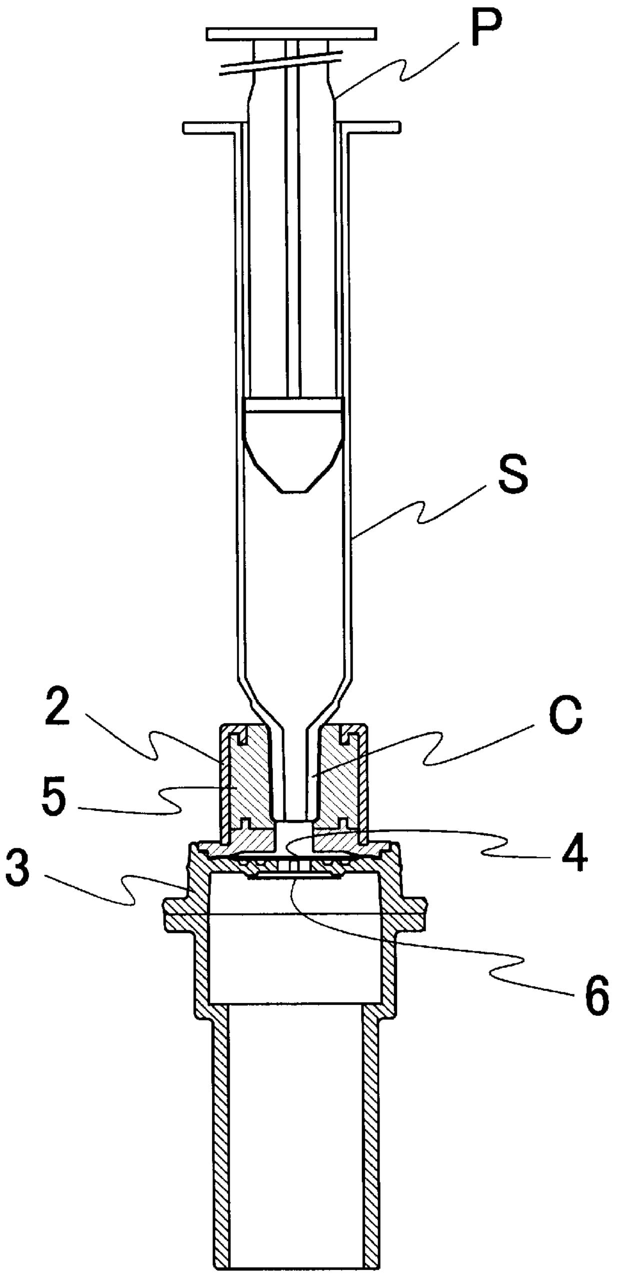
FIG. 3 is a cross sectional view of the infusion container shown in FIG. 1 showing a top end tip of a syringe attached to a communication port of the infusion container.

The slit 51 which is closed but allows the top end tip C of the syringe S to pass therethrough is formed substantially at a central part of the rubber stopper 5 and from the top end to the base end of the rubber stopper 5 as shown in FIG. 3. Further, numeral "24" denotes a protection seal for preventing contamination of the communication port 2. As the protection seal 24, sterile paper, aluminum film or plastic film or the like may be generally adopted.

The communication channel 31 is an inner lumen of the communication channel portion 3 which is made of the same material as that of the communication port 2 and is formed cylindrically in general. The communication channel portion 3 may be connected integrally with the communication port 2 by an appropriate method, for example, heat welding, as shown in FIG. 2.

The communication channel 31 is a channel for providing communication between the inner lumen 21 of the communication port 2 and the inside of the container main body 1. An annular protrusion 32 is provided adjacent to the top end portion of the inner wall of the communication channel part 3, which is the connection end with the communication port 2. A surface on a base end of the annular protrusion 32 is perpendicular to an axis connecting the top end of the communication channel 31 to the base end thereof. A film as the closing means 6 is attached to the surface of the base end of the annular protrusion 32 and is capable of being easily opened. Further, an annular rib 321 as shown in FIG. 2 may be provided on the surface of the base end of the annular protrusion 32. In a case that the annular rib 321 is provided on the annular protrusion 32, the film as the closing means 6 is welded with the annular rib 321.

The closing means 6 is preferably a film having chemical resistance and is welded directly to the annular protrusion 32 or easily releasably to the annular rib 321 provided on the annular protrusion 32. A check valve may also be adopted as the closing member 6, but it is necessary to change the structure of the communication channel portion 3. As the material for forming the film, a polymer blend of a material for forming the communication channel portion 3 and a resin not having compatibility therewith is generally adopted. For example, in a case where the material for forming the communication channel portion 3 is polyethylene, a polymer blend of polyethylene and polypropylene is suitably used as the material for forming the film. The blending ratio of the polyethylene and polypropylene is preferably from 3:7 to 7:3 in this case.

A sterilization filter 4 is sandwiched between the communication port 2 and the communication channel portion 3 so that bacteria or foreign bodies in drug solutions to be injected into the container main body 1 from the communication port 2 are removed by the sterilization filter 4. As the sterilization filter 4, a membrane filter is preferably adopted and filters, for example, of the depth type or anisotropic type may also be adopted. In a case of using the membrane filter, the pore diameter of the membrane of the sterilization filter 4 is desirably 0.45 $\mu$m or less, and more preferably, 0.22 $\mu$m or less so as to inhibit permeation of bacteria. As the material for forming the sterilization filter 4, cellulose acetate, regenerated cellulose, cellulose ester, polyamide, polytetrafluoroethylene, polyolefin or the like can be adopted.

An embodiment of a method of using the infusion container according to this invention will hereinafter be described.

At first, the protection seal 24 as shown in FIG. 2 is removed from the communication port 2 of the infusion container. Then, the top end tip C of a syringe S is inserted through the slit 51 of the rubber stopper 5 in the communication port 2 as shown in FIG. 3. In this case, the top end tip C passes through the slit 51 of the rubber stopper 5 and the top end of the top end tip C is exposed to the communication channel 31. After that, when the plunger P of the syringe S is pushed to discharge a drug solution such as a vitamin preparation or the like filled in the inside of the syringe S, the drug solution permeates the sterilization filter 4 and reaches the closing means 6, i.e., the film in FIG. 3, and a space between the rubber stopper 5 and the closing means 6 is filled with the drug solution. Then, since the closing member 6 is pressed from the top end with the same force as the force with which the plunger P is pressed, the closing means 6 is detached from the annular rib 321 providing communication between the inside of the syringe S and the inside of the container main body 1 and the drug solution in the syringe S is injected into the container main body 1. After the completion of the injection of the drug solution in the syringe S into the container main body 1, the top end tip C of the syringe S is removed from the rubber stopper 5. Finally, an infusion tube set, a catheter or the like is connected to the discharge port 7, so that the drug solution injected and mixed in the container main body 1 can be administered to a patient.

EFFECTS OF THE INVENTION

Since a sterilization filter is provided in the drug communication channel in the infusion container of the present invention, a drug solution in a syringe is capable of being aseptically injected into the infusion container. Further, since the communication port in the infusion container of the present invention is closed with a rubber stopper having a slit and the top end tip of the syringe is inserted through the slit, coring does not occur. Further, since the number of components of the infusion container of the present invention is small, the infusion container has a compact structure.

What is claimed is:

1. An infusion container comprising a communication port for connecting with a syringe, a container main body, a communication channel for providing communication between an inside of the container main body and an inner lumen of the communication port, a sterilization filter provided in the communication channel, a rubber stopper closing the communication port and having an openable slit formed therein for allowing a top end tip of the syringe to pass therethrough and a closing means closing the communication channel, wherein said communication channel is an inner lumen of a communication channel portion, an annular protrusion is arranged on an inner wall of the communication channel, said closing means is disposed at a base end of the sterilization filter and is a film welded weakly to a surface of said annular protrusion, and said sterilization filter is sandwiched between the communication port and the communication channel portion.

* * * * *